(12) United States Patent
Erickson et al.

(10) Patent No.: US 6,923,319 B1
(45) Date of Patent: Aug. 2, 2005

(54) SHARPS CONTAINER FOR SAFE TRANSPORTATION AND DISPENSING OF UNUSED PEN NEEDLE ASSEMBLIES AND FOR SEQUENTIAL SAFE STORAGE OF USED PEN NEEDLES

(75) Inventors: Thomas E. Erickson, Crosslake, MN (US); James J. Erickson, Mound, MN (US); Timothy A. Bachman, Saint Paul, MN (US)

(73) Assignee: ULTI Med Inc., St. Paul, MN (US)

( * ) Notice: Subject to any disclaimer, the term of this patent is extended or adjusted under 35 U.S.C. 154(b) by 0 days.

(21) Appl. No.: 10/862,622

(22) Filed: Jun. 7, 2004

(51) Int. Cl.⁷ .................. B65D 85/24; B65D 83/02
(52) U.S. Cl. ......................... 206/366; 206/370
(58) Field of Search .............. 206/363–366, 206/370, 817; 220/908; 221/36, 37, 40, 45, 221/101; 604/110, 403

(56) References Cited

U.S. PATENT DOCUMENTS

| | | | |
|---|---|---|---|
| 5,046,614 A * | 9/1991 | Torres et al. ............... | 206/366 |
| 5,409,113 A | 4/1995 | Richardson et al. | |
| 5,469,964 A * | 11/1995 | Bailey ........................ | 206/370 |
| 5,494,158 A | 2/1996 | Erickson | |
| 5,545,145 A | 8/1996 | Clinton et al. | |
| 5,603,404 A * | 2/1997 | Nazare et al. ............... | 206/366 |
| 5,971,966 A | 10/1999 | Lav | |
| 6,685,017 B2 | 2/2004 | Erickson | |
| 6,745,898 B2 * | 6/2004 | Lin ............................. | 206/366 |
| 6,792,662 B2 * | 9/2004 | Samuel ........................ | 604/110 |

\* cited by examiner

*Primary Examiner*—Luan K. Bui
(74) *Attorney, Agent, or Firm*—Roger W. Jensen

(57) ABSTRACT

A sharps container for (i) the safe storage and dispensing of unused pen needle assemblies and (ii) a safe means for receiving used pen needles and ejecting same into the container. The container comprises a housing within which is rotatably mounted a used pen needle receiving and ejecting means. Used pen needles are inserted into the receiving means. The receiving and ejecting means is rotated and, during the rotation, cam follower means connected to the ejecting means engages cam means within the housing to cause the ejection of the used pen needle into the housing. The housing also has a separate storage space for unused pen needle assemblies. Alternate structures provide for withdrawal of unused pen needle assemblies for dispensing. The dispensing can be done on a serial basis where the pen needle assemblies which are attached to a flexible tape for serial withdrawal from the housing through an exit opening. The dispensing can also be done on a bulk basis where a plurality of unused pen needle assemblies are transferred through the exit opening at the same time.

27 Claims, 7 Drawing Sheets

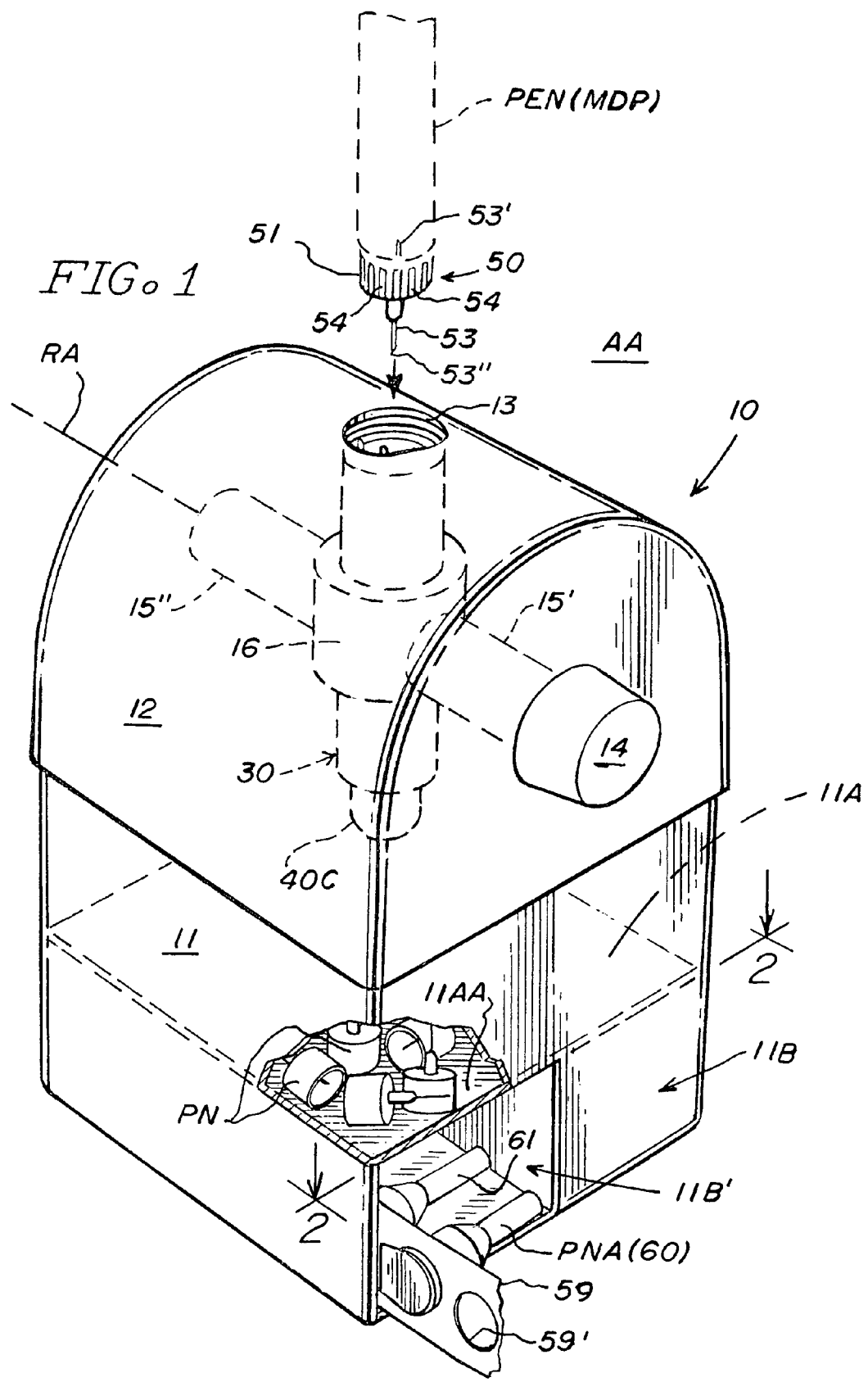

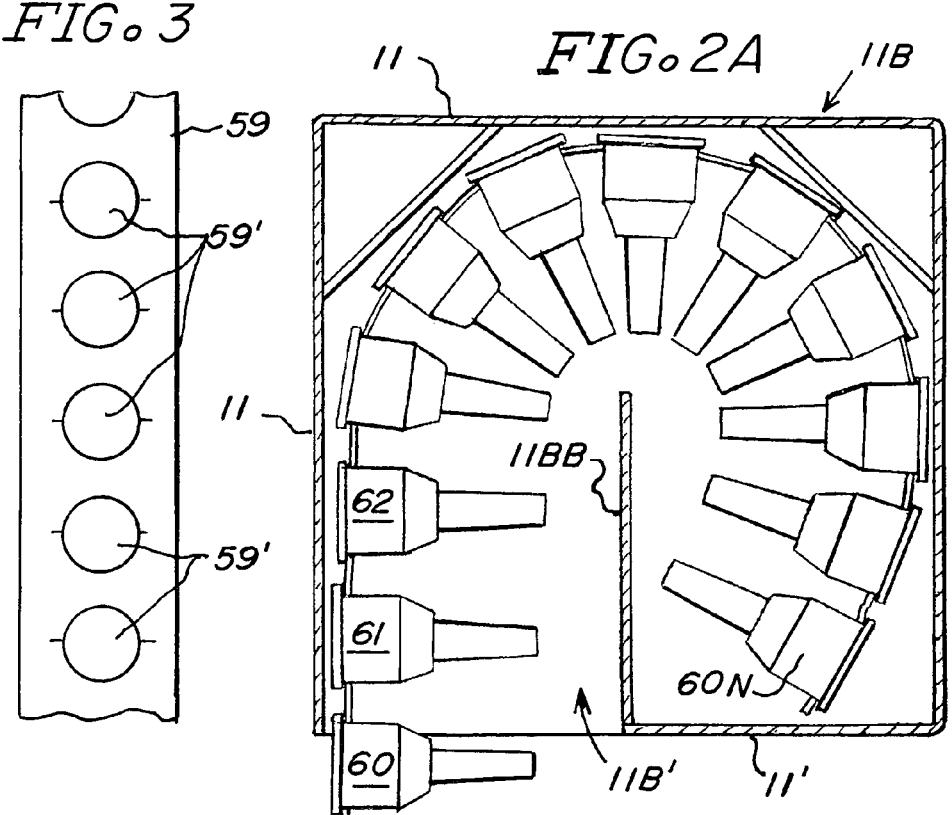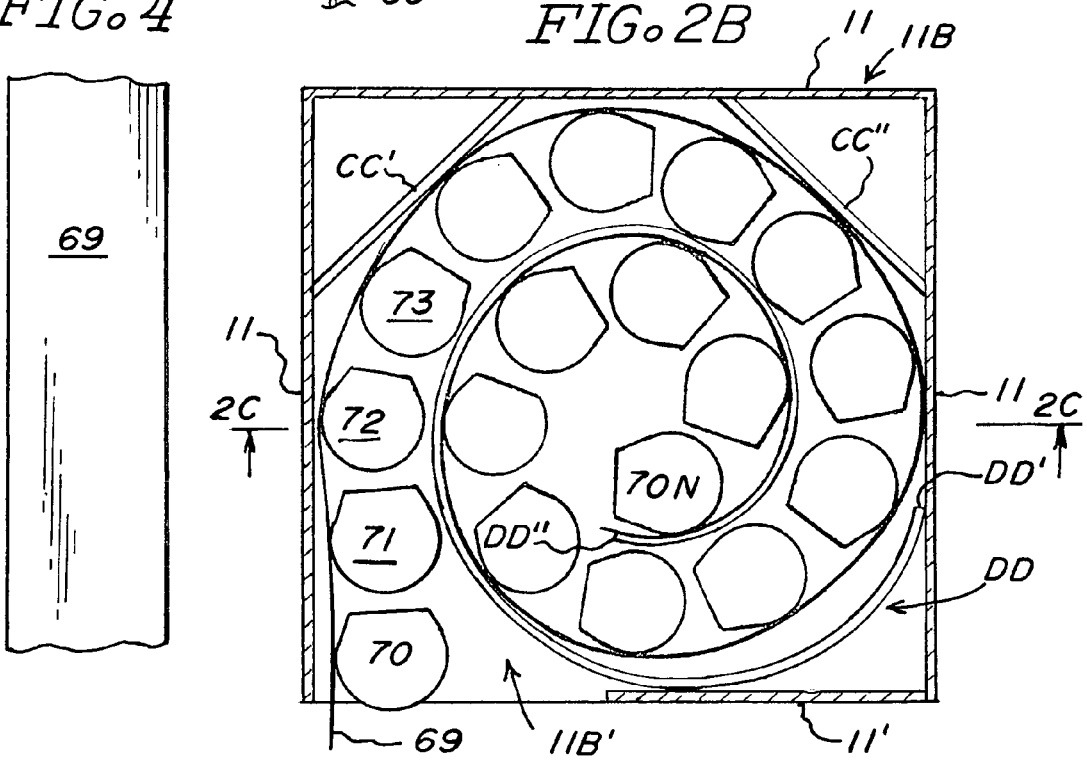

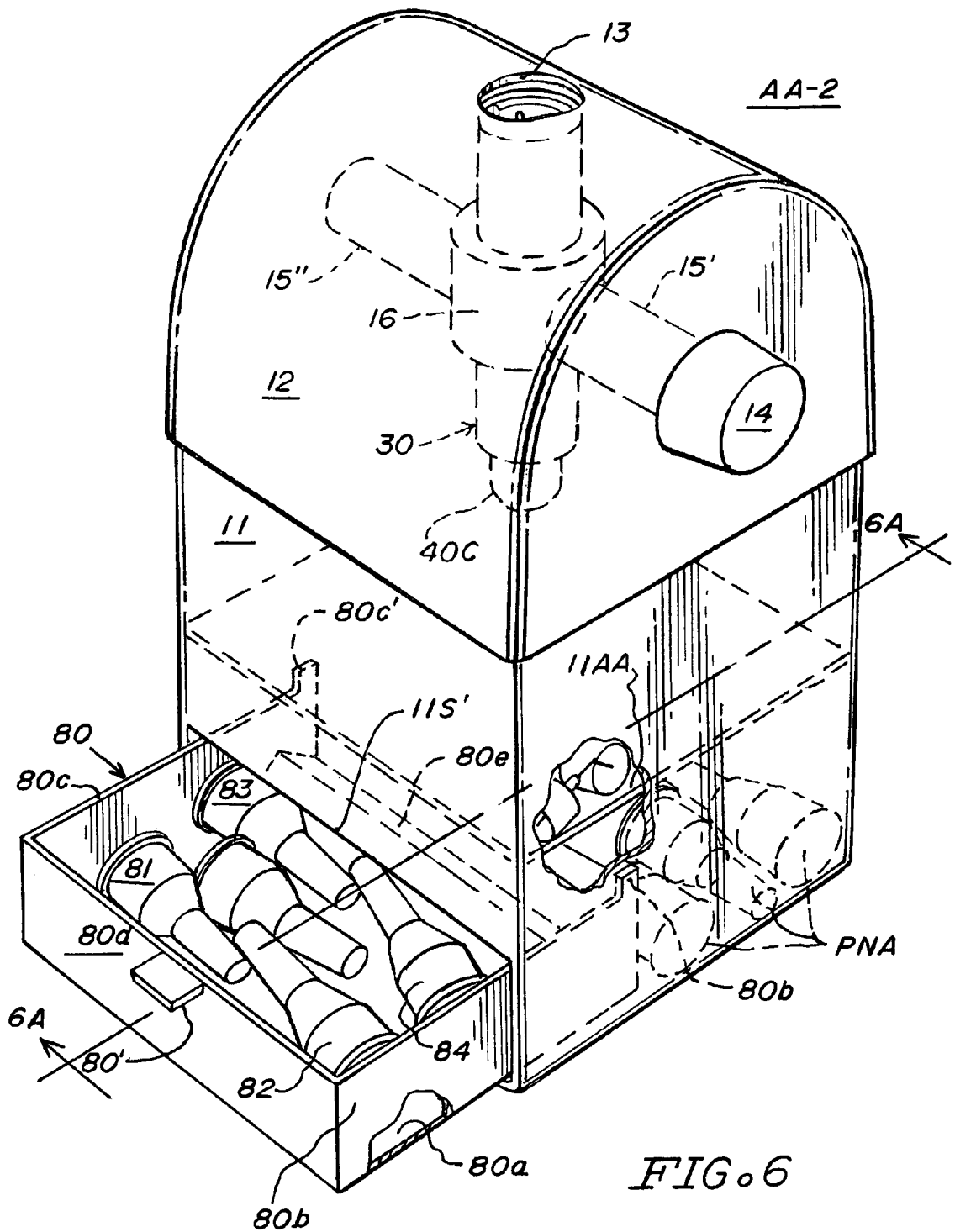

SHARPS CONTAINER FOR SAFE TRANSPORTATION AND DISPENSING OF UNUSED PEN NEEDLE ASSEMBLIES AND FOR SEQUENTIAL SAFE STORAGE OF USED PEN NEEDLES

BACKGROUND AND FIELD OF THE INVENTION

This invention provides a multipurpose "sharps" container. A first function is the disposal of used pen needles (sometimes hereafter referred to as "PNs") and specifically to a sharps container for used PNs which provides the safe (no-touch) sequential insertion of used PNs into the container for safe storage therein. The invention, importantly, also provides for safe, convenient transportation of a plurality of unused pen needle assemblies (PNAs) within the same sharps container (but hygienically isolated from the used PNs) and for dispensing said unused PNAs from the sharps container. Embodiments of the invention provide for "bulk" dispensing of unused PNAs.

Because of well known health issues, the safe disposal of syringes and other "sharps" has long been a high priority for medical related and other facilities. Prior art sharps containers are found, for example, in venues such as hospitals, medical clinics, and retail and other non-medical establishments. These containers are usually securely attached to some base means and have a lock means to permit controlled and safe removal of used "sharps."

There are also prior art "portable" sharps containers for syringes, examples being U.S. Pat. Nos. 5,494,158 and 6,685,017, which show sharps containers which necessarily are large because of the elongated syringes.

Medical delivery pens (sometimes hereafter "MDPs") have, more recently, become widely used instead of, or in addition to, syringes, e.g., by diabetics, who frequently inject themselves several times a day with accurately measured, adjustable, pre-selected amounts of insulin or other medication. Medical delivery pens include a reservoir of medication and a distal end adapted to be attached (usually by thread means) to a pen needle assembly (PNA). As is well known (see, for example FIG. 1 of U.S. Pat. No. 5,545,145), the pen needle assembly has (within an outer, generally cylindrical shield 28) a generally cylindrical housing 26 within which is mounted an axially extending hollow needle 21, (i) the proximal end 24 of which punctures a seal in the distal end 16 of the medical delivery pen 10 (to allow the flow there-through of medication) when the delivery pen is screwed into the proximal end of the pen needle cylindrical housing 26, and (ii) the distal end 22 of which is for insertion into tissue of the person requiring the medication. The pen needle assemblies typically include a removable thin sterile seal covering the proximal (large diameter) end of the said outer shield and a removable tube-like shield covering the distal portion of the hollow needle. The assembled pen needle assembly is then factory sterilized. The user of a pen needle assembly removes the seal from the outer shield, screws the pen into the proximal end of the pen needle housing, removes the outer and tube-like shields, sets the medical delivery pen for the desired dose of medication, and then inserts the distal end of the pen needle into the target tissue following which the medical delivery pen is actuated to deliver the desired dose of medication through the hollow needle into said tissue.

Many diabetics routinely administer medication to themselves several times a day by injection of a pre-selected quantity(ies) of insulin (or substitute medication) in liquid form; the correct amount of medication can be determined from prior professional medical instruction or by use of convenient portable blood analysis kits which are small, compact and provide rapid indicators of the user's blood sugar level. The several daily injections are often done away from the diabetic's home or residence which has made the use of the portable, convenient medical delivery pens widespread. The aforesaid testing kits and the medical delivery pens are relatively small in size and can easily fit within a woman's purse or equivalent. A typical scenario for a diabetic at a restaurant for a meal is to first use the blood sugar testing kit to obtain an indicator of his or her blood sugar level. This information then facilitates programming or adjusting the medical delivery pen to deliver the desired quantity of medication. Then the pen with an attached PN (a PNA sans the outer protective shield) is used to inject the medication. These steps require a relatively short length of time and can be done with minimum loss of privacy.

Some users who require multiple daily injections of medications use, selectively, both medical syringes and medical delivery pens (MDPs). For example, a diabetic may use a medical syringe (with a pre-selected amount of medication) at the beginning of the day and then shift to MDPs for subsequent injections that day because of convenience for use outside of their residence and also some users feel less discomfort from a PN injection as compared to that from a syringe needle-type injection.

MDPs are also widely used by doctors, nurses and other professionals in their duties. Many individuals will request (sometimes insist) that an injection be done with a pen needle rather than a syringe. The aforementioned professionals are especially mindful of possible dangers from a needle stick and the possible unwanted "sticks" that occur.

In a perfect world, the user (both individual and professional) of a pen needle assembly would, after the first use of a pen needle, carefully detach the used PN from the MDP and safely dispose said PN. An approved disposal procedure is (i) insertion of the distal end of the needle into the tube-like shield (sometimes omitted) and thence the shielded PN cylindrical housing into the outer shield (thus returning to a PNA configuration), (ii) unscrewing the MDP from the proximal end of the pen needle cylindrical housing, and (iii) careful placement of the used PN (in a PNA configuration) into a safe sharps container.

Alas, the recommended procedure is not always followed. Used (and potentially dangerous) PNs or PNAs are routinely left in unsafe places where innocent third parties may unwittingly be "stuck." Examples (frequently outrageous) of such unsafe places are purses, the pockets on the back of aircraft seats, private and public wastebaskets, garbage cans, dumpsters and empty milk containers or other improvised and unsafe containers.

Further, the above described disposal procedure requires that the user (or associate) handle or hold the PN while the pen is unscrewed therefrom; this creates the possibility of a potentially dangerous stick Also, if the user (or associate) tries to insert the PN into the outer shield to form a PNA, then additional handling is again required with the possibility of a "stick"

One prior art example of a container for unused and used pen needle assemblies is U.S. Pat. No. 5,545,145 which shows a tube containing a small number of unused pen needle assemblies arranged in axial alignment. This patent also teaches that, as unused assemblies are removed from one end of the tube, then a used assembly may be inserted into the tube from the other end. The tube is adapted to be attached to the side of a medical delivery pen. This arrangement has significant shortcomings. The capacity is quite limited and, potentially dangerous "sticks" could occur when a user (or associate) tries to insert a used PN (with or without the protective outer shield) into the used end of the tube.

SUMMARY OF THE INVENTION

The present invention provides (i) a totally "no-touch" means for a user of a PNA to safely transfer a used PN from a MDP into a unique container for safe storage therein without, as indicated, any touching of the used PN by the user, (ii) hygienically separate safe transportation and storage of unused PNAs within the same unique container and (iii) means for controlled dispensing of said unused PNAs via an exit opening in said container. Additionally certain embodiments of our invention provide for sharps containers which, in addition to the function of safe storage of used PNs, have means for safe dispensing of bulk quantities of unused PNAs; this is a function which has special applicability in clinics and the like where large numbers of unused PNAs are required for daily requirements.

This invention provides a sharps container for safe manual, sequential "feeding," or disposal of used PNs into the container for safe storage therein. The container is a housing with an internal storage space sized to hold a plurality of used PNs. A used PN receiving and ejecting means is provided within the housing and includes (i) manually rotatable means connected to the housing for rotation about an axis, (ii) an ejector assembly connected to the manually rotatable means (to rotate therewith about the axis) and including a cam follower means, and (iii) cam means on the housing positioned to contact and actuate the cam follower means upon rotation of the manually rotatable means, the "actuation" of the cam follower means causing the "ejection" of the PN into the container for safe storage.

Importantly, our invention also provides a sharps container which is especially useful for an individual such as a diabetic who may require several daily doses of medication, which doses are required throughout the day (frequently at meal time) and thus may occur at the users residence but are often at other locations such as the user's place of work, at a restaurant, in an automobile or aircraft, etc. Thus, the container has a convenient supply of unused PNAs to be used as required as well as the aforementioned means for the safe disposal of used PNs. Several different arrangements are shown for the storage and dispensing of unused PNAs. The container conveniently can be relatively compact and sized to fit within a woman's purse or equivalent. Alternately, the container can be sized larger to facilitate the storage therein of a large number of unused PNAs and, further, can be structured to dispense unused PNAs either sequentially or in bulk.

BRIEF DESCRIPTION OF THE DRAWINGS

FIG. 1 is a top, side isometric view of a preferred embodiment of a PN sharps container provided by the invention.

FIG. 2A is a view of a plurality of PNAs connected to a flexible tape and coiled in an unused PNA storage compartment in the container of FIG. 1 as viewed along section lines 2—2 thereof.

FIG. 2B is a view similar to that of FIG. 2A (but for an alternate preferred embodiment of the invention) with a plurality of unused PNAs attached to a tape means but oriented 90 degrees from the orientation of the PNAs in FIG. 2A.

FIG. 3 is a plan view of the tape means 59 used with the PNAs depicted in FIG. 2A.

FIG. 4 is a plan view of the tape means 69 used with the PNAs depicted in FIG. 2B.

FIGS. 5, 6, and 7 show, respectively, our invention with alternate means in the bottom portion of the housing means for the storage and dispensing of unused PNAs.

DETAILED DESCRIPTION OF THE INVENTION

Figure 6A:
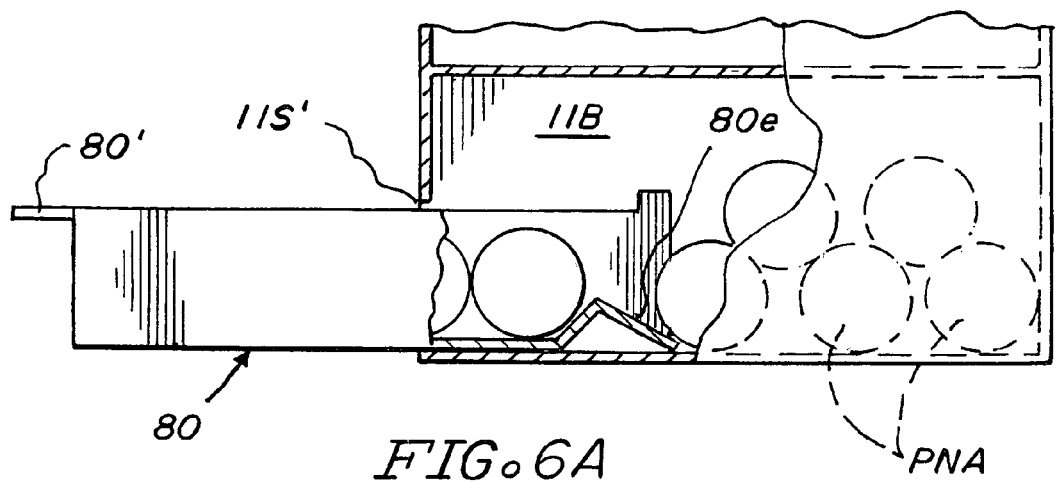
FIG. 6A is a cross-sectional view of a drawer means 80 for dispensing unused PNAs as viewed along section lines 6A—6A of FIG. 6.

FIG. 1 shows a sharps container AA having a means for the safe, i.e., "no direct human touching" storage of used pen needles. The container comprises a housing 10 having a first or bottom storage and dispensing portion 11 and a second or upper cover portion 12 which fit together as shown. The first portion 11 is, in turn, divided into two parallel oriented portions 11A and 11B by a partition 11AA integral with portion 11 and positioned to facilitate (i) the safe storage of a plurality of used PNs and (ii) the safe storage and dispensing of unused PNAs as is shown in FIG. 1.

Cover portion 12 of the housing means 10 has a curved shape about a rotational axis RA. The top of the cover 12 has an opening 13 sized to permit the axial insertion therethrough of a used pen needle PN identified in the drawings by reference numeral 50

FIG. 1 also shows, in phantom, a medical delivery pen (MDP) which is representative of the well known types currently used and having at the distal end thereof male thread means for attachment to female threads in the proximal end of a pen needle 50. It should be assumed that pen needle 50 shown in FIG. 1 has already been used and the user desires to safely remove the used pen needle from the pen and thence place the used pen needle into safe storage means. The pen needle 50 has a cylindrical surface 51 with a pre-selected outer diameter. The cylindrical surface also has a plurality of longitudinally extending shallow grooves 54 which co-act with radially extending ribs of a used pen needle receiving and ejecting assembly 30 to hold the pen needle against rotation about its longitudinal axis when the user unscrews the MDP therefrom. Additional specific details of the used pen needle receiving and ejecting assembly 30 and its associated coacting apparatus are shown in our copending application filed on even date herewith and having Ser. No. 10/862,621; the disclosure of same is incorporated herein for reference. Set forth below is a summary of the details and functions of the used pen needle receiving and ejecting assembly.

A manually rotatable means comprising an external knob 14 with connected shafts 15' and 15" and a central collar 16 rotatably supported by bearing means in end walls of the housing cover 12 section for rotation, relative to the housing, about a rotational axis RA. The collar 16 has a central bore sized to receive and firmly hold the used pen needle receiving and ejector assembly 30 and additionally has means for attachment thereto of the inboard ends of shafts 15' and 15".

Thus manual rotation of the knob 14 will rotate the ejector assembly 30 about the rotational axis RA.

The ejector assembly 30, for this embodiment, is shown to comprise a first member or elongated tubular member having first and second ends. The total axial length of the elongated tubular member is pre-selected, regard being given to the dimensions of the cover section 12, so that the tubular member may be rotated about the rotational axis without contacting the inside surface 12 of the housing but yet have the used pen needle receiving end thereof sufficiently adjacent to the opening 13 to provide the used pen needle receiving function.

An elongated ejector means has a pre-selected axial length and a cylindrical shape sized to slidably fit within the elongated tubular member for relative axial movement therewith; a rounded cam follower end 40C of the ejector means being shown in FIG. 1. It is important to note that end 40C of the ejector means normally, i.e. initially, extends a pre-selected distance beyond one end of the tubular member as is shown in FIG. 5A. The terms "normally" and "initially" cover the case when the cam follower end 40C is not in contact with its co-acting cam means. The co-acting cam means is positioned within and fixed to the cover section 12 and may, in fact, be the inside curved surface of cover section 12. Additional details regarding the cam follower-cam function are available in our above mentioned co-pending application.

Thus, rotation of the knob 14 (and thus the entire used pen needle receiving and ejecting means 30) causes contact by the cam follower 40C with the aforesaid cam means to force the ejector means axially within the elongated tubular member to push, i.e. eject a used pen needle out from its received position into the used pen needle storage portion 11A.

It will be understood that the pen user does not have to touch the used pen needle either to (i) remove the used pen needle from the pen, or (ii) dispose the used pen needle into a safe storage means.

The unused PNA storage and dispensing portion 11B of the housing is shown in several, alternate configurations. The first is shown in FIG. 2A. One of the side walls 11' of storage section 11B includes an exit opening 11B' and an internal side wall 11BB to permit withdrawal of unused PNAs 60, 61, 62 . . . 60N attached to a flexible tape means 59 by being positioned in serial, spaced apart holes 59' in the tape as is shown in FIG. 3. FIG. 2A shows clearly the PNAs within the storage space, coiled around side wall 11BB, and exiting at opening 11B'. FIG. 1 also shows the tape 59 with connected PNAs 60 et seq. available, upon demand, to the MDP user at exit opening 11B'; the user of the unused PNAs pulls on the end of the tape 59 to receive the desired number of unused PNAs.

Figure 2C:
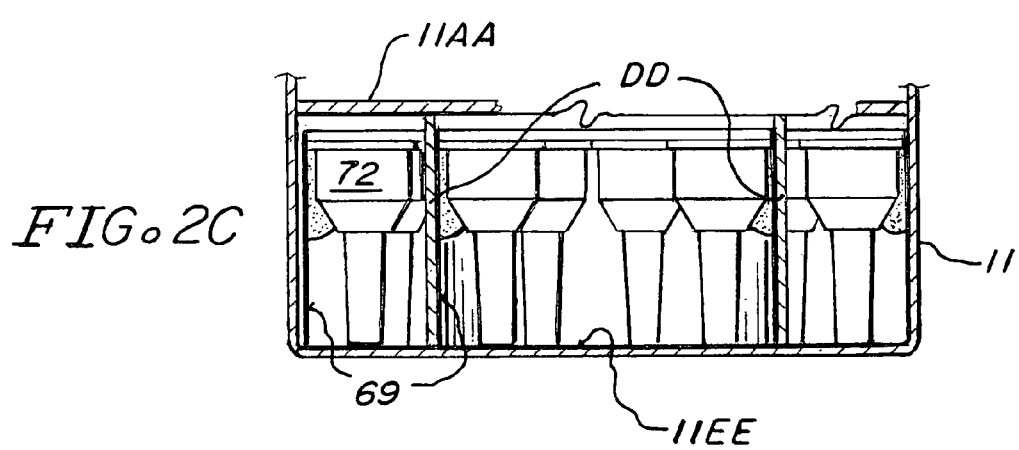
FIG. 2C is a cross-sectional view of FIG. 2B as viewed along section lines 2C—2C thereof.

An alternate unused PNA storage and dispensing configuration 11B is shown in FIGS. 2B and 2C. Again, a side wall 11' has an exit opening 11B'. Within the storage and dispensing portion 11B are (i) a pair of angled interior walls CC' positioned in the corners as shown and (ii) a spiraled guide means D1) having a first end DD' attached to a side 11 of the portion and a second end DD'' generally centrally positioned in the portion. A plurality of unused PNAs (70, 71, 72, 73 . . . 70N) are depicted connected in a serial, spaced-apart configuration to a tape 69. The tape 69 with attached PNAs is configured in a coil and is shown following the spiral guide means DD. The PNAs may be attached to the tape 69 by suitable means such as an adhesive, the cylindrical sides of the PNAs being the zone of attachment to the tape. The spiral guide means DD thus facilitates the loading and dispensing of unused PNAs into and out of the storage space.

Other configurations for the storage and dispensing the unused PNAs also may be used. The configuration depicted in FIGS. 2B and 2C has an advantage of an increased number of PNAs being storable in a given container footprint as compared to that of FIG. 2A.

It will be noted that the configurations depicted in FIGS. 1–2C are especially useful in the sequential dispensing of unused PNAs, the user pulling out only the next available PNA. However, the user could pull out several PNAs if that were desired.

The following embodiments of our invention facilitate the simultaneous safe dispensing of a plurality of unused PNAs from the sharps container; for some applications such as use in a clinic, this function can be very desirable.

Figure 5:
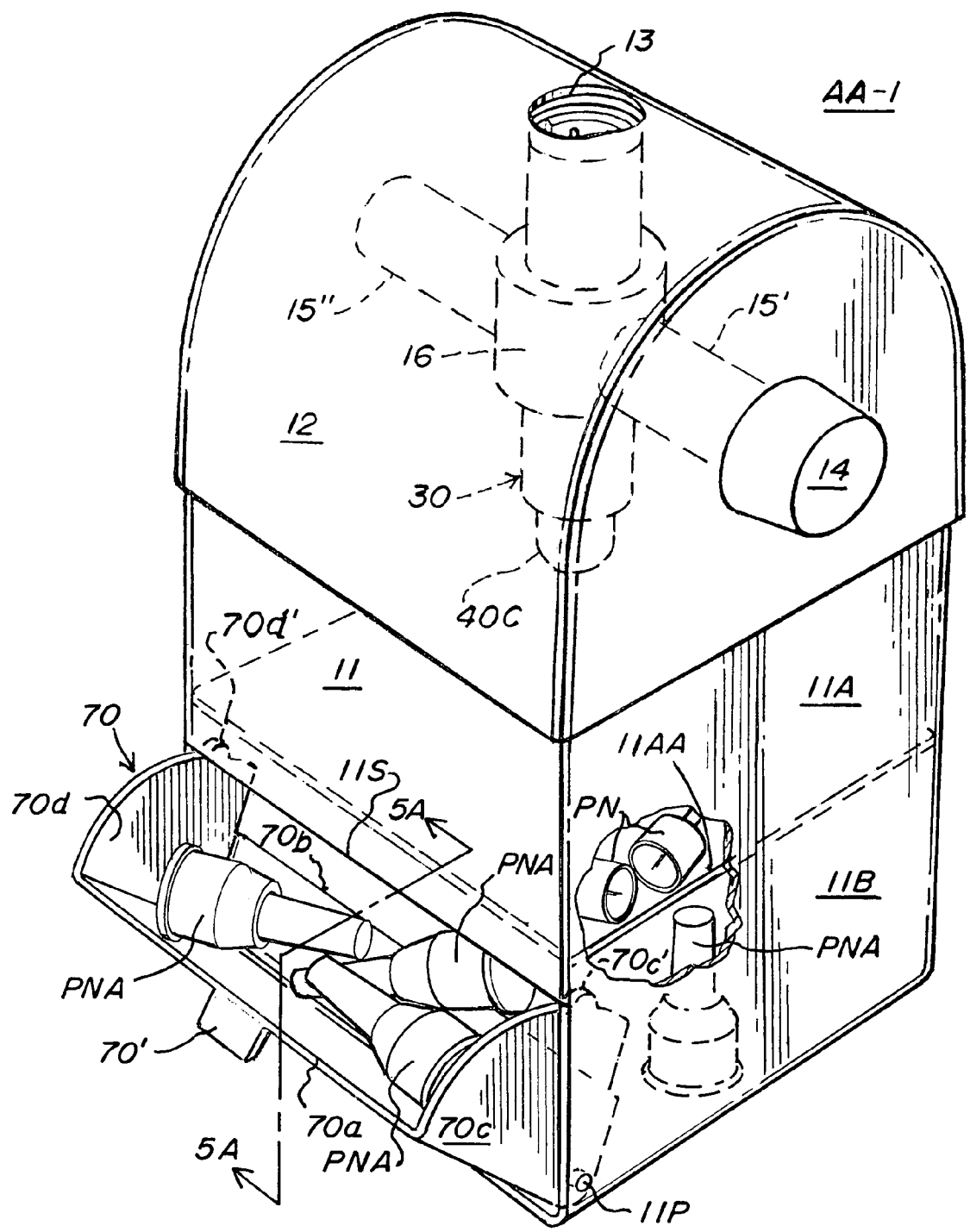
Figure 5A:
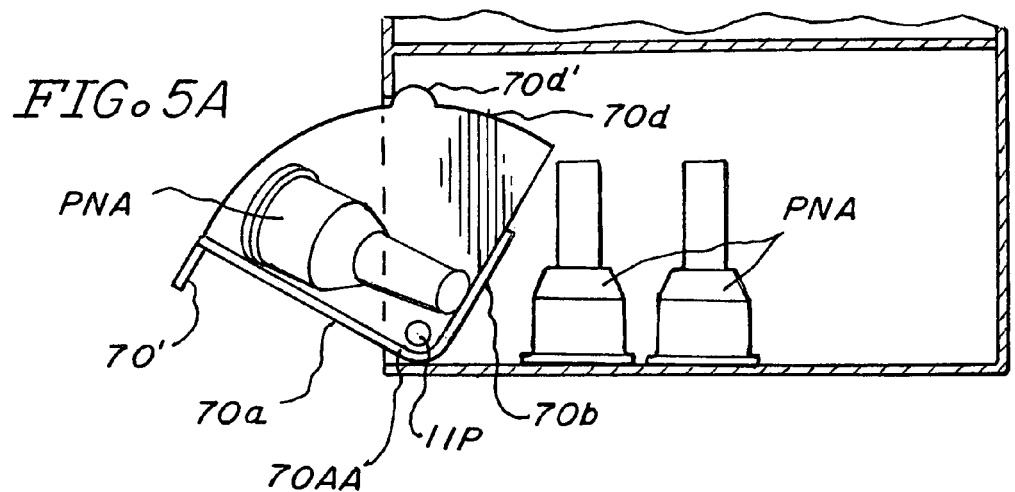
FIG. 5A is a cross-sectional view of a bin means for dispensing unused PNAs as viewed along section lines 5A—5A of FIG. 5.

FIG. 5 shows a sharps container AA-1 which is very similar to container AA shown in FIG. 1; it has the same used PN receiving, ejecting and storage means as container AA. However, the unused PNA storage and dispensing means is different; it is configured to facilitate the dispensing of more than one unused PNA at the same time, i.e., a means to provide unused PNAs in bulk quantities.

Thus container AA-1 has a housing means with partition 11AA separating used PN storage portion 11A from unused PNA storage and dispensing portion 11B. An exit opening 11S at the left side of portion 11B (as viewed in FIG. 5) is provided, within which is a bin-like member 70 is rotatably positioned. Bin member 70 has (i) two angularly-displaced-apart longitudinally extending surfaces 70a and 70b, joined at 70AA to form a V-shaped cross section as is shown in FIG. 5A and (ii) end surfaces means 70c and 70d to form a unitary pocket means sized to hold a plurality of unused PNAs. Bin member 70 is supported by bearing means 11P so that it may be manually rotated (by use of a tab 70') between an open or dispensing position as shown in FIG. 5 and a closed position where surface 70a is coplanar with the side 11 of the housing. When bin member 70 is in the closed position, additional unused PNAs may be transferred into said pocket as can be seen in FIG. 5A. End surface means 70c and 70d have stop means 70c' and 70d' to limit the outward rotation of the bin member 70.

FIG. 6 depicts another sharps container AA-2 having the same used PN receiving, ejecting and storage means as container AA of FIG. 1 but providing an alternate, multiple unused PNA dispensing apparatus. Thus container AA-2 has partition 11AA for defining used PN storage portion 11A and unused PNA storage and dispensing portion 11B. An exit opening 11S' at the left side of portion 11B (as viewed in FIG. 6) is provided and is sized to admit the transverse motion of a drawer 80 in and out of the housing to an unused PNA dispensing position shown in FIG. 6. The drawer has a bottom 80a, two sides 80b and 80c, a front 80d (with transversely extending pull tab 80'), and back ramp-like means 80e. Stop means 80c' and 80d' on the sides of the drawer limit the outward travel thereof. In operation, the drawer, holding unused PNAs 81, 82, 83 and 84, may be manually pulled out (by the user using tab 80') from portion 11B to the position shown in FIG. 6 to allow the user to remove said unused PNAs. Manual closing of the drawer 80 results in the front 80d being coplanar with the side 11 of the housing and, importantly, the ramp means 80e, as the drawer is closing, coacts with unused PNAs in portion 11b to transfer some into the drawer for additional dispensing to a user as is clearly shown in FIG. 6A.

Figure 7A:
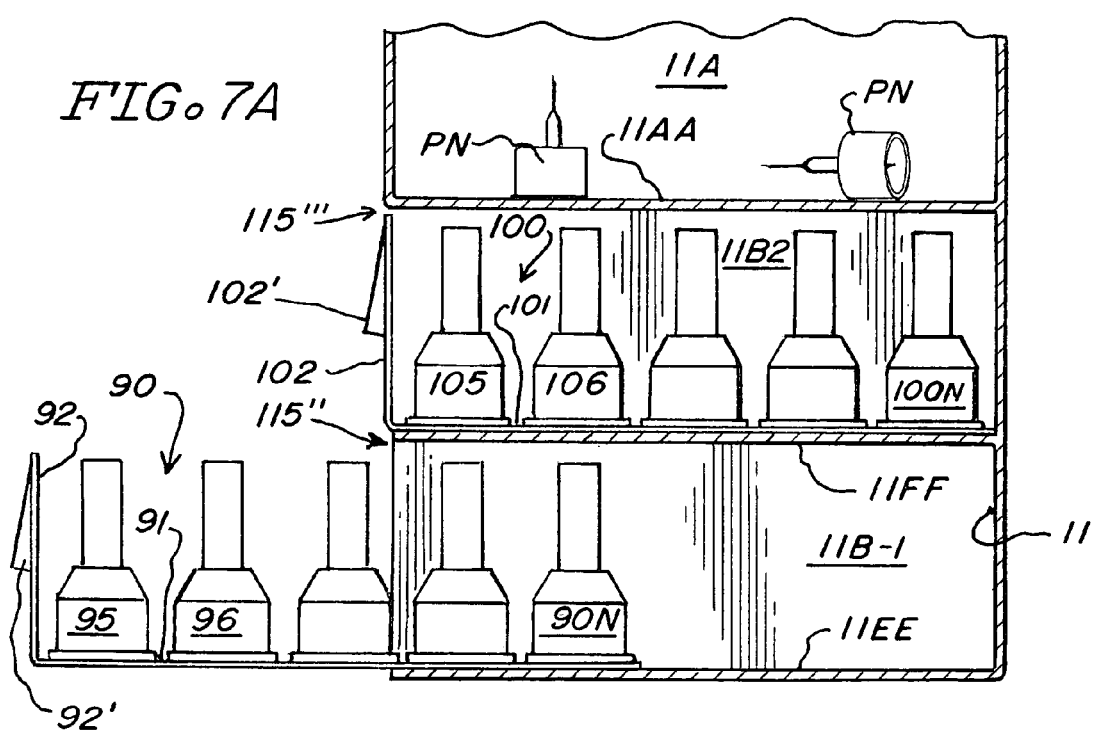
FIG. 7A is a cross-sectional view of the unused PNA storage and dispensing means of the sharps container AA-3.
Figure 7:
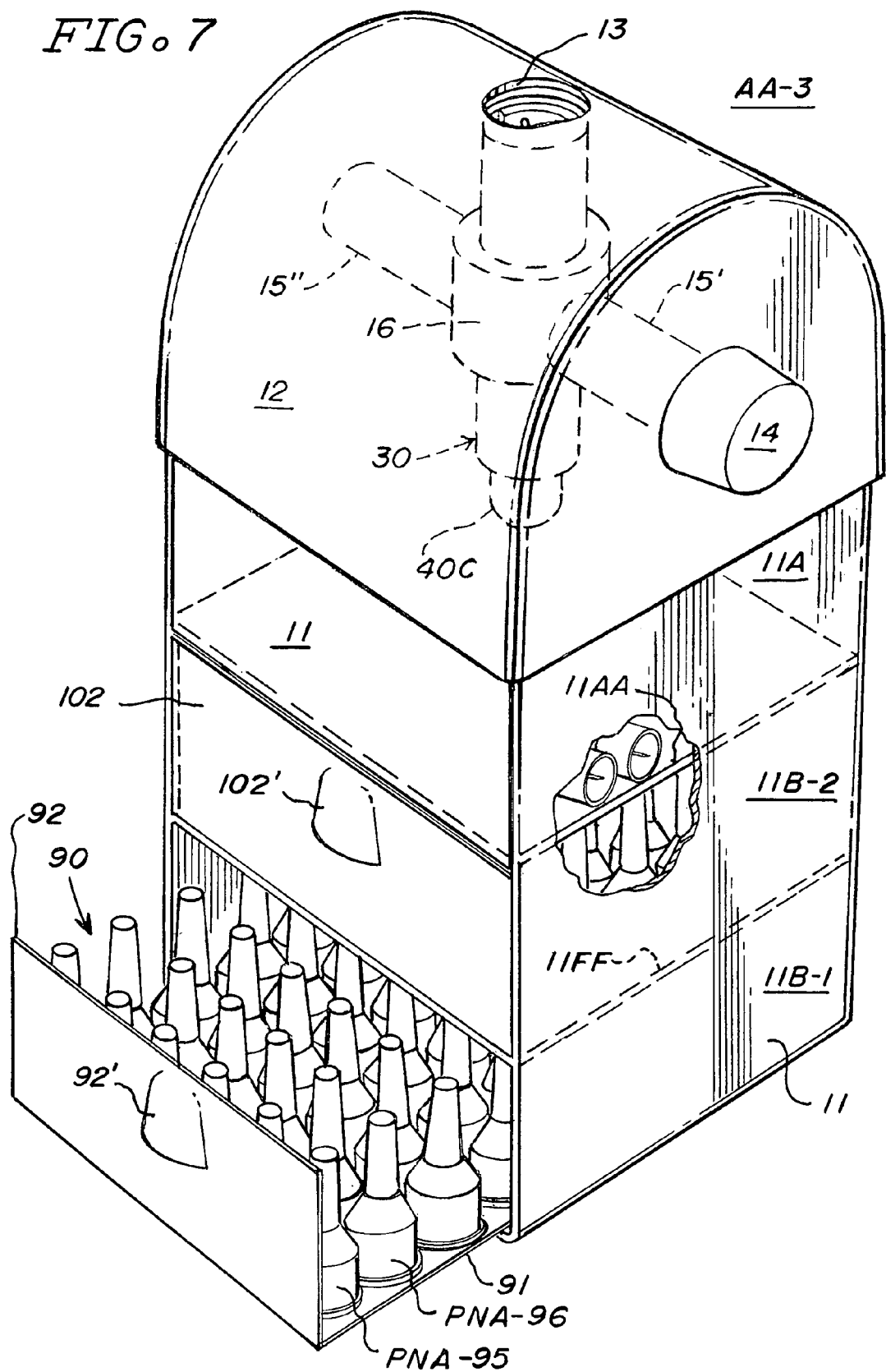

Another embodiment of our invention is the sharps container AA-3 depicted in FIGS. 7 and 7A which also uses the same used PN receiving, ejecting and storage means as container AA. Partition 11AA again defines the used PN storage portion 11A; however the unused PNA portion is divided into two sub-portions 11B-1 and 11B-2 defined by a partition 11FF integral with side 11 of the housing and extending parallel to the bottom 11EE of the housing (best shown in FIG. 7A). The vertical height of the sub-portions is pre-selected to allow for the storage of unused PNAs arranged with the proximal ends thereof abutting the bottom members 91 and 101 of a pair of tray means 90 and 100 respectively. Tray 90 also has a front 92 sized to match the exit opening 115″ between members 11EE and 11FF. Tray 100 also has a front 102 sized to match the exit opening 115‴ between members 11A and 11FF. Fronts 92 and 102 have engagement means 92′ and 102′ respectively for facilitating the manual withdrawal of the trays from the housing means.

A large number of unused PNAs are positioned on each of trays 90 and 100. Tray 90 has PNAs 95, 96 . . . 90N and tray 100 has PNAs 105, 106 . . . 100N; the PNAs, as indicated, are preferably oriented with the proximal ends abutting their respective trays. The PNAs may be secured by a suitable adhesive means to the trays. This orientation of the PNAs permits a maximization of the number of unused PNAs for a given size container.

While we have shown our preferred embodiments of the invention, it will be understood that variations may be made without departing from the inventive concept. Accordingly, the invention is to be limited only by the scope of the following claims.

What is claimed is:

1. A sharps container for facilitating (i) the safe transportation of a large number of unused pen needle assemblies, (ii) the safe dispensing of said unused pen needle assemblies from said container and (iii) the safe manual, sequential feeding of used pen needles into said container for safe storage therein, said pen needles having a cylindrical shape and a pre-selected outer diameter, said container comprising:
   A. a housing means sized to hold, in a bottom portion thereof, a plurality of unused pen needle assemblies, said housing having a bottom portion exit opening for facilitating the withdrawal there through of unused pen needle assemblies;
   B. means within said housing means for receiving and storing used pen needles; and
   C. used pen needle receiving and ejecting means connected to said housing means and including:
      (1) manually rotatable means connected to said housing means for rotation relative to said housing means about an axis,
      (2) an ejector assembly connected to said rotatable means to be rotated thereby about said axis, said ejector assembly comprising (i) an elongated member having recessed means at a first end thereof sized to receive a used pen needle and (ii) an ejector means connected to said elongated member for relative axial movement therewith and having cam follower means at one end thereof initially positioned a preselected distance beyond a second end of said elongated member, and
      (3) cam means connected to and within said housing positioned for contacting said cam follower means when said rotatable member and said ejector assembly is rotated about said axis to thereby move said ejector means axially with respect to said elongated member toward said first end of said elongated member so that a second end of said ejector means provides a pen needle ejecting motion;
   whereby, when a pen needle is positioned in said recessed means and said manually rotatable means is rotated about said axis sufficiently so that said cam follower means contacts and follows said cam means, said ejector means will force said pen needle axially out of said recessed means into said means within said housing for receiving and storing used pen needles.

2. The sharps container of claim 1 wherein said elongated member comprises tube means of pre-selected axial length having first and second ends and an internal bore within which is positioned said ejector means.

3. The sharps container of claim 1 further including an insertion opening in said housing sized to admit the axial insertion of a used pen needle therethrough.

4. The sharps container of claim 3 wherein said ejector assembly is selectively oriented about said axis by rotation of said manual rotatable means between (i) an initial position with said recessed means being positioned adjacent to and in alignment with said insertion opening to facilitate the axial insertion therethrough of an used pen needle into said recessed means, and (ii) a second position whereat said cam follower means engages said cam means, following which additional rotation of said ejector assembly about said axis causes the ejection of a used pen needle from said recessed means into said housing for safe storage therein.

5. The sharps container of claim 1 including a plurality of unused pen needle assemblies attached, in spaced-apart, series relationship, to a coiled, flexible tape means and positioned in said bottom portion of said housing means so that said unused pen needle assemblies may be dispensed through said exit opening.

6. The sharps container of claim 1 including a plurality of unused pen needle assemblies positioned in said bottom portion of said housing means and means for dispensing said unused pen needle assemblies through said bottom portion exit opening.

7. The sharps container of claim 5 wherein said pen needle assemblies each comprise an outer cylindrical shield, a cylindrical surface, and a proximal end.

8. The sharps container of claim 7 wherein said tape means has a plurality of serial, spaced-apart openings sized to receive said outer cylindrical shields of said pen needle assemblies.

9. The sharps container of claim 7 wherein said cylindrical surfaces of said pen needle assemblies are attached to said flexible tape means.

10. The sharps container of claim 7 wherein said pen needle assemblies are attached to said flexible tape means with said proximal ends thereof being adjacent to said flexible tape means.

11. The sharps container of claim 6 wherein said means for dispensing said unused pen needle assemblies dispenses said unused pen needle assemblies sequentially.

12. The sharps container of claim 6 wherein said means for dispensing said unused pen needle assemblies dispenses a plurality of unused pen needle assemblies.

13. A sharps container for facilitating (i) the safe storage and transportation of a large number of unused pen needle assemblies stored within said container, (ii) the safe dispensing of said unused pen needle assemblies from said container and (iii) the safe, sequential disposal of used pen needles into said container for safe storage therein, said pen needles having a cylindrical shape and a pre-selected outer diameter, said container comprising:

A. a housing means sized (i) to hold in storage for dispensing, in a first portion thereof, a plurality of unused pen needle assemblies, said housing having a first portion exit opening and including means for facilitating the withdrawal therethrough of unused pen needle assemblies and (ii) to receive for storage, in a second portion thereof, used pen needles, said housing having partition means separating said first and second portions; and B. used pen needle receiving and ejecting means including (i) an ejector assembly rotatably connected to said housing means for rotation about an axis, said ejector assembly comprising (a) a first member having recessed means at a first end thereof sized to receive a used pen needle and (b) an ejector means connected to said first member for relative axial movement therewith and having cam follower means at one end thereof initially positioned a pre-selected distance beyond a second end of said first member, (ii) cam means connected to and within said housing means and positioned for contacting said cam follower means when said ejector assembly is rotated about said axis to thereby move said ejector means axially with respect to said first member toward said first end of said first member so that a second end of said ejector means provides a pen needle ejecting motion and (iii) means for manually rotating said ejector assembly about said axis relative to said housing means;

whereby, when a pen needle is positioned in said recessed means of said first member and said ejector assembly is rotated about said axis sufficiently so that said cam follower means contacts and follows said cam means, said ejector means will force said pen needle axially out of said recessed means into said means within said housing for receiving and storing used pen needles.

14. The sharps container of claim 13 wherein said first member comprises tube means of pre-selected axial length having first and second ends and an internal bore within which is positioned said ejector means.

15. The sharps container of claim 13 further including a used pen needle insertion opening in said housing sized to admit the axial insertion therethrough of a used pen needle.

16. The sharps container of claim 15 wherein said ejector assembly is selectively oriented about said axis by rotation of said manual rotatable means between (i) an initial position with said recessed means being positioned adjacent to and in alignment with said used pen needle insertion opening to facilitate the axial insertion therethrough of an used pen needle into said recessed means, and (ii) a second position whereat said cam follower means engages said cam means, following which additional rotation of said ejector assembly about said axis causes the ejection of a used pen needle from said recessed means into said second portion of said housing for safe storage therein.

17. The sharps container of claim 13 including (i) a plurality of unused pen needle assemblies positioned in said first portion of said housing means and (ii) means for dispensing a plurality of unused pen needle assemblies from said first portion of said housing mean through said first portion exit opening.

18. The sharps container of claim 17 wherein said means for dispensing a plurality of unused pen needle assemblies includes a bin member rotatably connected to said first portion of said housing means, sized to hold a plurality of unused pen needle assemblies, and manually movable between a closed position and an open position.

19. The sharps container of claim 17 wherein said means for dispensing a plurality of unused pen needle assemblies includes tray means having a first position within said first portion of said housing means, adapted to hold thereon a plurality of unused pen needle assemblies, and supported by said first portion of said housing means for relative transverse/lateral movement therewith to a second position whereat at least a portion of said tray means is outside of said first portion of said housing means whereat unused pen needle assemblies are positioned for dispensing and use.

20. The sharps container of claim 19 wherein said plurality of unused pen needle assemblies each (a) comprise an outer cylindrical shield, a cylindrical surface and a proximal end and (b) are mounted on said tray means with said proximal ends thereof abutting said tray means.

21. The sharps container of claim 17 wherein said means for dispensing a plurality of unused pen needle assemblies includes a plurality of unused pen needle assemblies attached, in spaced-apart, series relationship, to a coiled, flexible tape means.

22. The sharps container of claim 19 including a plurality of said tray means each adapted to hold a plurality of unused pen needle assemblies.

23. The sharps container of claim 18 wherein said bin member has means for receiving unused pen needle assemblies when said bin member is in said closed position and for positioning said unused pen needle assemblies for dispensing and use when said bin member is in said open position.

24. The sharps container of claim 17 wherein said means for dispensing a plurality of unused pen needle assemblies from said first portion of said housing means comprises an unused pen needle receiving member, movably connected to said housing means, proximate to said first portion exit opening, and movable between a first position for receiving said unused pen needle assemblies, thence through said first portion exit opening to a second position for dispensing of said unused pen needle assemblies.

25. The sharps container of claim 24 wherein said unused pen needle receiving member comprises a bin means rotatably connected to said housing means and positioned in said first portion exit opening.

26. The sharps container of claim 24 wherein said unused pen needle receiving member comprises tray means.

27. The sharps container of claim 24 wherein said unused pen needle receiving member comprises a plurality of tray means.

* * * * *